United States Patent [19]

Carson

[11] 4,167,535

[45] Sep. 11, 1979

[54] ISOPARAFFIN-OLEFIN ALKYLATION UTILIZING LIQUEFIED NORMAL PARAFFIN CONCENTRATE IN THE REACTION VESSEL

[75] Inventor: Don B. Carson, Mt. Prospect, Ill.

[73] Assignee: UOP Inc., Des Plaines, Ill.

[21] Appl. No.: 899,601

[22] Filed: Apr. 24, 1978

[51] Int. Cl.² .............................................. C07C 3/54
[52] U.S. Cl. .................................... 585/717; 585/715; 585/719; 585/723
[58] Field of Search ........................ 260/683.48, 683.59, 260/683.61, 683.62, 683.58, 683.49, 683.45

[56] References Cited

U.S. PATENT DOCUMENTS

| | | | |
|---|---|---|---|
| 2,409,389 | 10/1946 | Ringham | 260/683.45 |
| 2,906,796 | 9/1959 | Putney | 260/683.48 |
| 2,949,494 | 8/1960 | Putney | 260/683.58 |
| 3,055,958 | 9/1962 | Webb, Jr. | 260/683.58 |
| 3,080,438 | 3/1963 | Sailors | 260/683.48 |
| 3,105,102 | 9/1963 | Webb, Jr. | 260/683.58 |
| 3,969,078 | 7/1976 | Zabransky | 260/683.48 |

Primary Examiner—George Crasanakis
Attorney, Agent, or Firm—James R. Hoatson, Jr.; Robert W. Erickson; William H. Page, II

[57] ABSTRACT

Field butanes, otherwise introduced into an isostripping column, also utilized to recover alkylate product from unreacted isobutane, are separately fractionated to provide an isobutane concentrate and a normal butane concentrate. The former is increased in pressure and reacted with the olefinic feed stream in admixture with HF-acid catalyst. The latter is introduced into the reaction zone wherein it is vaporized via indirect contact with the reaction mixture. Vaporous normal butane is introduced into the fractionation facility wherein the exothermic heat of reaction serves to separate the field butane stream. Alkylation reactions can thus be conducted at sub-ambient temperatures which results in an alkylate product of improved quality. This technique also obviates the necessity for a cooling water system, thus eliminating the possibility of HF-acid contamination of water bodies.

10 Claims, 1 Drawing Figure

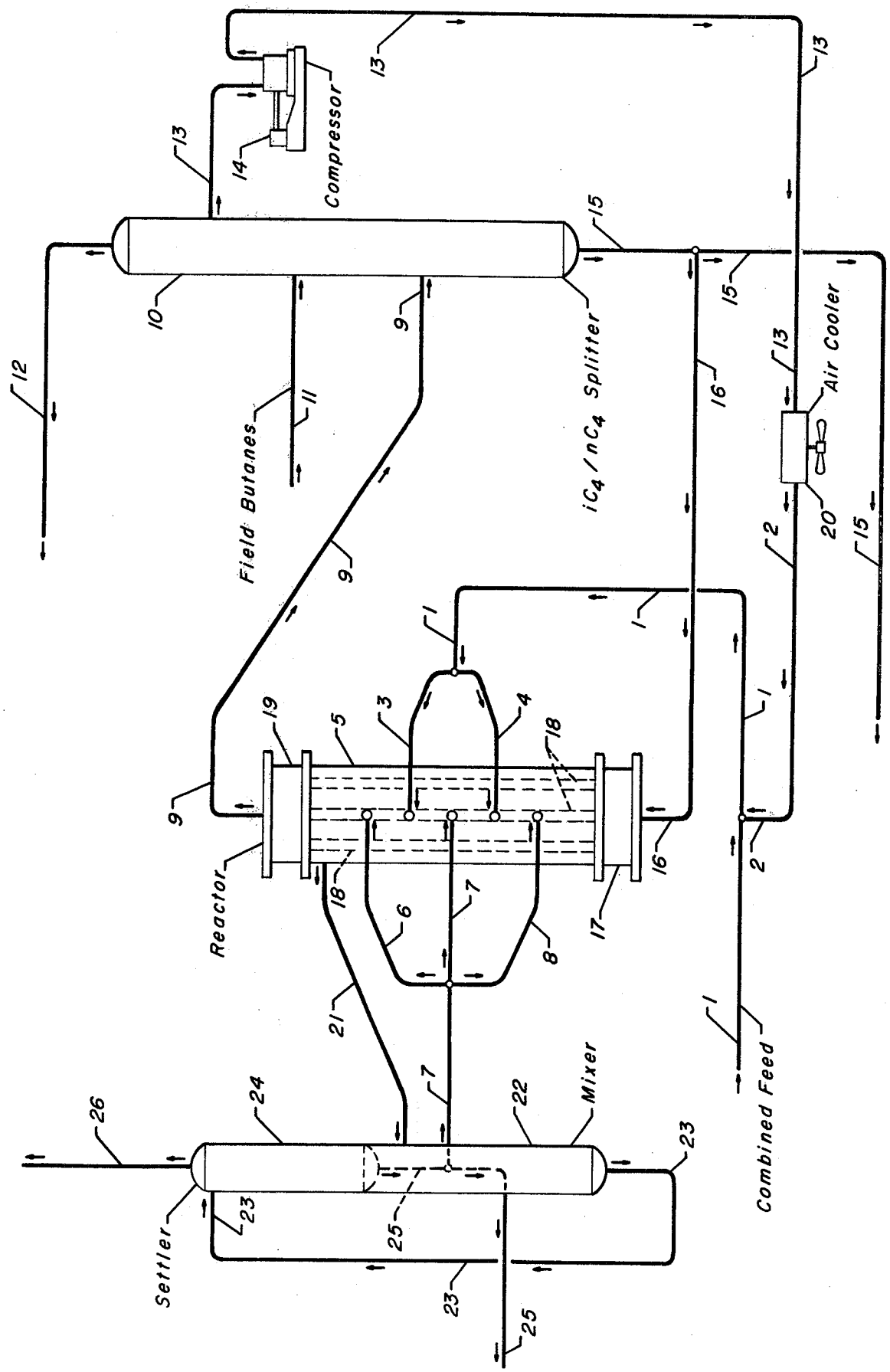

ISOPARAFFIN-OLEFIN ALKYLATION UTILIZING LIQUEFIED NORMAL PARAFFIN CONCENTRATE IN THE REACTION VESSEL

APPLICABILITY OF INVENTION

As described herein, the present inventive concept directs itself to, and encompasses a process for effecting the HF-acid catalyzed reaction of an isoparaffin with an olefin to produce a normally liquid motor fuel alkylate. Such a reaction was developed more than 35 years ago in order to meet the ever-increasing demands for staggering quantities of high-octane motor fuels having enhanced anti-knock properties. Since the advent thereof, the HF alkylation process has experienced a multitude of changes and improvements with respect to unit design and operating techniques. Suitable isoparaffins are those having four to about seven carbon atoms per molecule, including isobutane, isopentane, neopentane, one or more isohexanes and various isoheptanes. Similarly, the olefinic feed stream contains from three to about seven carbon atoms per molecule, and includes propylene, 1-butene, 2-butene, isobutylene, the isomeric amylenes, hexenes, heptenes and mixtures. For all practical purposes, the greater majority of HF alkylation processes employ isobutane with the olefinic material being either propylene, butylenes, or mixtures thereof.

Many innovations in HF alkylation have been directed toward the cooling of the reaction mixture. Such is mandatory due to the exceptionally high degree of exothermicity which accompanies alkylation reactions. An anomaly exists since lower reaction mixture temperatures —e.g. 50° F. to 70° F.—versus the more commonly employed higher temperature of around 100° F. creates significantly more favorable results. As an example, alkylate product quality is improved; high molecular weight polymeric material (commonly referred to as "tar") formation is inhibited and reduced; and, the isobutane to olefin ratio in the reaction chamber can be reduced. In its basic conceptual form, the present invention directs itself not only at this desirable reduction in reaction mixture temperature, but also at the advantageous utilization of the exothermic heat of reaction which is wasted in conventional designs.

OBJECTS AND EMBODIMENTS

A principal object of the present invention is to provide a method which affords a lower temperature of the reaction mixture in HF-acid catalyzed alkylation of an isoparaffin with an olefin. As a corollary objective, improved alkylate quality is achieved in a more economical, trouble-free fashion.

Another object is to make possible the control of the reactor temperature at a level lower than that which could be attained through the use of ambient temperature water as a reaction mixture cooling medium.

Specifically, an object is to offer a technique which leads to reduced capital investment and operating costs, particularly with respect to major vessels, equipment and the off-site facilities associated with acid-catalyzed alkylation systems.

Therefore, in a broad embodiment, the present invention affords a process for the acid-catalyzed alkylation of an isoparaffin with an olefinic feed stream which comprises the steps of: (a) separating an isoparaffin/normal paraffin mixture at separation conditions selected to provide (i) an isoparaffin concentrate and, (ii) a normal paraffin concentrate; (b) increasing the pressure of said isoparaffin concentrate, reducing the temperature thereof and reacting said isoparaffin with said olefinic feed stream in admixture with an acid-acting catalyst, in a reaction vessel and at alkylation conditions selected to produce a normally liquid alkylate product; and, (c) introducing at least a liquefied portion of said normal paraffin concentrate into said reaction vessel and therein vaporizing said normal paraffin via indirect contact with the isoparaffin/olefinic hydrocarbon reaction mixture.

This embodiment is further characterized in that the normal paraffin concentrate is vaporous at normal conditions of 60° F. and atmospheric pressure.

In another, more specific embodiment, my invention affords an improvement in a process for the HF-acid catalyzed alkylation of isobutane with an olefinic feed stream, in which process a field butane stream, containing normal butane and isobutane, and an alkylated reaction effluent stream, containing unreacted isobutane, are separated in a common fractionation facility to (i) recover the normally liquid alkylate product, (ii) remove a normal butane concentrate from the alkylation system and, (iii) provide an isobutane concentrate for recycle to the alkylation reaction zone, which improvement comprises the steps of: (a) introducing said field butane stream into a separate fractionation system and therein separating said stream, at separation conditions selected to provide (i) an isobutane concentrate and, (ii) a normal butane concentrate; (b) increasing the pressure of said isobutane concentrate, reducing the temperature thereof and reacting said isobutane with an olefinic feed stream in admixture with HF-acid, in a reaction vessel and at alkylation conditions selected to produce a normally liquid alkylate product; and, (c) liquefying at least a portion of said normal butane concentrate, introducing the liquefied portion into said reaction vessel, and therein vaporizing said normal butane portion via indirect contact with the isobutane/olefinic hydrocarbon reaction mixture.

This embodiment is further characterized in that the temperature of the isobutane concentrate is preferably reduced through the use of ambient air.

Other objects and embodiments of my invention will become evident from the following more detailed description thereof. In one such other embodiment, the olefinic feed stream comprises propylene, butylenes, or a mixture thereof.

CITATION OF RELEVANT PRIOR ART

Candor compels recognition and acknowledgment of the fact that the prior art is replete with a wide variety of publications, inclusive of issued patents, directed toward the acid-catalyzed alkylation of an isoparaffin with an olefin to produce a normally liquid alkylate motor fuel product. This is particularly true with respect to hydrogen fluoride alkylation which traces its development over an approximate 35-year period. Any attempt to exhaustively delineate the HF alkylation art herein would constitute an exercise in futility. However, a brief description of several innovations, for the purposes of illustrating the particular area to which the present invention is applicable, is believed to be warranted. Copies of the specifically delineated U.S. patents accompany this application.

U.S. Pat. No. 3,080,438 (Cl. 260-683.48), issued Mar. 5, 1963, is principally directed toward HF alkylation effected in a so-called circulatory system wherein the hydrocarbon portion of the reactant stream becomes the continuous phase. A relatively large amount of the hydrocarbon phase recovered from the alkylation effluent (alkylate product and unreacted isobutane) is cooled and introduced into an acid cooler containing mixing means. The rate of the cooling medium employed to cool the portion of the hydrocarbon phase is regulated in direct response to the temperature sensed in the reaction conduit. The thus-cooled product, in admixture with fresh hydrocarbon charge stock is passed through the internal mixer, thereby picking up hydrogen fluoride from the surrounding volume in the acid cooler (Column 3, Lines 59–64). HF acid is withdrawn from a settler (17) on a ratio flow control, which also monitors the flow rate of the hydrocarbon feed, for introduction into the acid cooler.

It would appear that the greater proportion of the heat of reaction is removed by the voluminous portion of the cooled product hydrocarbon phase withdrawn from the settler (Column 4, Lines 48–52). This is nothing more than introducing the fresh feed (Lines 10 and 11) at a reduced temperature. The principal purpose for recycling the large quantity of product hydrocarbon is to create a hydrocarbon continuous phase.

A control system for regulating reaction zone temperature is presented in U.S. Pat. No. 3,969,078 (Cl. 23-253A), issued July 13, 1976, and is directed specifically to HF alkylation units having a mixed olefinic charge which is susceptible to fluctuations in composition. Essentially, the composition of the feed stream is analyzed, the octane rating of the ultimate alkylate product is determined and the temperature of the reaction mixture is sensed. Representative signals are developed and transmitted to computer/comparator means. The latter generates two signals, one of which is used to regulate the quantity of effluent recycle (line 42 from settler 13), the second being the regulation of the reactor cooling medium (line 9). Cumulative to U.S. Pat. No. 3,969,078 are the following U.S. patents: U.S. Pat. Nos. 3,929,926 (Cl. 260-683.48), issued Dec. 30, 1975; No. 3,937,749 (Cl. 260-683.48), issued Feb. 10, 1976; No. 3,948,603 (Cl. 23-253A), issued Apr. 6, 1976; No. 3,981,942 (Cl. 260-683.48), issued Sept. 21, 1976; and, No. 3,972,957 (Cl. 260-683.48), issued Aug. 3, 1976. Copies of these cumulative patents have not been filed with this application.

In U.S. Pat. No. 2,409,389 (Cl. 260-683.45), issued Oct. 15, 1946, alkylation of an isoparaffin with an olefin is effected utilizing a liquid hydrocarbon/aluminum chloride catalyst. A plurality (four) of reaction vessels are used in conjunction with a plurality of settlers (three). Alkylate-containing product (line 55) is introduced into separating means (60), from which di-isopropyl product (line 62), light gases (line 66), heavy alkylate (line 65), isobutane (line 63) and normal butane (line 64) are recovered. The isobutane is recycled to the alkylation system, while the normal butane is withdrawn therefrom. Normal butane enters the process with the combined feed stream (line 11) and the make-up isobutane stream (line 10). Use of the normal butane stream in accordance with my inventive concept is not recognized.

U.S. Pat. No. 3,867,473 (Cl. 260-683.45), issued Feb. 18, 1975, directs itself to a two reaction vessel system (5 and 14) in which all the isobutane (lines 4 and 30) is introduced into the first zone, whereas the olefinic feed stream is split (lines 2 and 3). An isostripping column is employed to recover alkylate product and isobutane for recycle, reject a propane concentrate and remove normal butane from the system (line 29). Reaction mixture temperature in both reaction vessels is maintained by absorbing the exothermic heat of reaction with cooling water (lines 6 and 15).

U.S. Pat. No. 2,906,796 (cl. 260-683.48), issued Sept. 29, 1959, is directed toward a two-stage process for acid alkylation of an isoparaffin with an olefinic feed stream. Applicable to both $H_2SO_4$-acid (FIG. 1) and HF-acid (FIG. 2) techniques, the process utilizes a closed cycle refrigeration system to cool one of the reaction stages and so-called "effluent refrigeration" to cool the second reaction stage. The former is acknowledged as old in the art, and utilizes ammonia or propane (Column 3, Lines 15–28). Effluent refrigeration is defined (Column 1, Lines 24–33) as any system employing all, or part of the product effluent issuing from a reaction vessel, or from the acid settler. With respect to FIG. 2, the effluent refrigeration technique is described at Column 10, Line 32 through Column 11, Line 12. Similarly, U.S. Pat. No. 2,949,494 (Cl. 260-683.58), issued Aug. 16, 1960, utilizes all of the hydrocarbon-rich reaction product effluent, at a reduced pressure, (after acid separation) as the reaction zone cooling medium.

Molecular sieve separation of normal paraffins, introduced into the alkylation system with the isoparaffin feed, for the removal thereof from the process, is the subject of U.S. Pat. No. 3,105,102 (Cl. 260-683.58), issued Sept. 24, 1963. It should be noted that the separation takes place after the normal paraffin has passed through the reaction zone as a component of the reaction mixture, and following the separation of the HF-acid from the reaction product effluent. The cooling medium thus includes (FIG. 1) the normally liquid alkylate product. In FIG. 2, the molecular sieve separation is effected after the hydrocarbon-rich portion of the reaction product effluent has been utilized as the indirect cooling medium. Closed cycle refrigeration, without identification of either the cooling medium, or the source thereof is used in the technique presented in FIG. 4.

U.S. Pat. No. 3,055,958 (Cl. 260-683.58), issued Sept. 25, 1962, offers an alleged improvement in the type of processes described in the last three delineated references. This improvement consists of an effluent (acid lean) flash system installed upstream from the commonly-utilized deisobutanizer. Flashed isobutane concentrate is condensed and re-introduced into the reaction vessel, while normal butane is removed in the deisobutanizer bottoms stream in admixture with the normally liquid alkylate product.

In the foregoing delineated references, and particularly the last four which have been described, there is no recognition of the combination of (1) separating an isoparaffin feed stream to remove normal paraffins, (2) compressing and cooling the isoparaffin prior to its introduction into the reaction zone, (3) liquefying the normal paraffin and vaporizing the same via indirect contact with the reaction mixture, thereby absorbing the exothermic heat of reaction, and, (4) utilizing the heat of reaction to separate the original isoparaffin/normal paraffin mixture. Actually, the foregoing represents the type of HF alkylation processes to which the present invention is most applicable.

SUMMARY OF INVENTION

As hereinbefore stated, the present invention is intended to be integrated into an acid-catalyzed alkylation unit for the production of a normally liquid motor fuel alkylate (having seven or eight carbon atoms per molecule). In the interest of brevity, the invention and process will be further described with respect to the alkylation of isobutane with a olefinic feed stream containing both propylene and mixed butylenes, and utilizing hydrofluoric acid catalyst. Since both internal (isobutane recycle) and external (field butanes) streams, including the olefinic charge say from a coking unit, will contain some paraffinic material, such will appear in the reaction mixture. Hydrogen fluoride is utilized in an amount sufficient to provide an acid/hydrocarbon volume ratio, in the reaction vessel, of from about 0.5:1.0 to about 3.0:1.0. Generally, commercially available anhydrous hydrogen fluoride will be charged to the alkylation system as fresh catalyst. It is possible to use hydrogen fluoride containing as much as about 10.0% water; however, excessive dilution is undesirable since it tends to reduce the activity of the catalyst while introducing severe corrosion problems into the system.

To reduce the tendency of the olefinic components of the feedstock to undergo polymerization prior to alkylation, the molar proportion of isoparaffin to olefinic hydrocarbon within the reaction zone is maintained at a value greater than 1.0:1.0, up to about 20.0:1.0, and preferably from about 3.0:1.0 to about 15.0:1.0. Other alkylation conditions include temperatures in the range of about 0° F. ($-17.8°$ C.) to about 200° F. ($93°$ C.); maximum temperatures are preferably not above 110° F. ($43°$ C.) and the minimum temperature is at least about 30° F. ($-1.1°$ C.). Alkylation pressures are sufficiently high to maintain the reaction mixture in liquid phase; that is, from about 15.0 psi. (1.05 kg/sq.cm.) to about 600 psi. (42.2 kg/sq. cm.). Contact time in the alkylation reaction vessel is conveniently expressed in terms of a space-time relationship which is defined as volumes of HF-acid catalyst within the reaction zone divided by the volume rate per minute of hydrocarbon reactants charged to the reaction zone. The space-time relationship will be less than about five minutes, and preferably less than about two minutes.

It is understood that the precise operating conditions employed for a given alkylation system is not limiting upon the present invention which directs itself to a unique technique of controlling and maintaining the temperature of the reaction mixture. Hydrocarbon alkylation reactions are highly exothermic, and every conceivable means is employed to maintain and control the reaction mixture temperature at that level which is consistent with the character of the reactant feed, other operating conditions and the desired quality of the ultimate alkylate product. Where the isoparaffin is isobutane and the olefinic feed stream is a mixture of propylene and the butylenes, the precise temperature at which the reaction mixture will be best maintained is principally dependent upon the propylene/butylene ratio as well as the 1-butene/2-butene/isobutene ratio.

Alkylation reaction vessels are designed along lines similar to tube-and-shell heat-exchangers; the reaction mixture, including the HF-acid, traverses the shell side, while a cooling medium traverses the tube side in one or more passes. In a few alternative designs, only the HF-acid phase passes through the heat-exchanger in amounts so great that subcooling of this acid phase will inhibit the temperature rise in the subsequent reaction zone. In this type of system, the reaction zone may simply be a pipe or small pressure vessel. Thus, HF-acid from the acid settler passes into the cooler, the isobutane/olefinic feed is admixed with the cooled HF-acid and the mixture reintroduced into the acid settler.

Many intricate designs have been proposed, both from the standpoint of the removal of the heat of reaction and intimate mixing of the reactant stream components and the HF acid. Regardless of the vessel design employed, the cooling medium functions via indirect contact with the reaction mixture. A perusal of the prior art indicates that most commercialized alkylation systems utilize refinery cooling water to absorb the exothermic heat of reaction in maintaining reaction temperature. In general, the available refinery cooling water is at best "warm"; that is, at some temperature in excess of about 60° F., say about 80° F. to about 95° F. Since the exit temperature of the water employed to remove the exothermic heat of reaction is limited by the maximum temperature at which the reaction is to be conducted, and since the maximum temperature is desirably low, the quantity of heat removed by a given amount of cooling water is limited to the sensible heat available over a small temperature rise. Thus, extremely large quantities of cooling water are required in order to maintain the reaction mixture at its lowest possible temperature.

As a general rule, therefore, the quality of the final normally liquid alkylate product is limited by the cooling water inlet temperature. That is, alkylate quality improves with decreasing reaction mixture temperature. Obviously, the reaction mixture temperature cannot be less than the cooling water inlet temperature; at best, the minimum reaction temperature will approach the cooling water inlet temperature only within about 10° F. to about 20° F.

The process encompassed by the present inventive concept, is founded upon recognizing (1) the inadequacies attendant the utilization of available refinery cooling water in voluminous quantities and, (2) that a readily-available material exists which can be substituted to significant economic and techical advantages. Considering those HF alkylation systems in which the isoparaffin is isobutane, two primary sources of isobutane supply exist. The first source is commonly referred to as "make-up isobutane," and which may be obtained as an item of commerce, subject to availability. Secondarily, isobutane is a major component of other refinery streams which are referred to in the HF alkylation art as "field butanes." Briefly referring to U.S. Pat. No. 3,969,078, hereinbefore described, the field butane stream (line 20) is introduced into the isostripping column (vessel 19), for separation therein along with the hydrocarbon-rich portion of the alkylation product effluent stream (line 18). The normal butane portion of the field butane stream is removed from the process (line 21), while the isobutane portion is recycled (line 2) to the alkylation reaction zone. In accordance with the present invention, the field butane stream otherwise introduced and separated in the isostripping column passes into a separate isobutane/normal butane splitter.

As previously stated, the field butane stream will contain some propane and possibly a minor quantity of lighter normally vaporous hydrocarbons. They will be withdrawn in the isobutane concentrated overhead stream from the $iC_4/nC_4$ splitting column, while the normal butane is withdrawn as the bottoms stream. The isobutane is increased in pressure, via compressive means, reduced in temperature and recycled to the reaction vessel as part of the combined reactant feed stream. At least a portion of the normal butane, in its liquid state is introduced into the tube side of the reaction vessel as aforesaid. Excess normal butane is withdrawn from the process as necessary. Vaporized normal butane from the reaction vessel is recovered and introduced into the isobutane/normal butane splitter.

Numerous advantages and beneficial results arise from the utilization of the liquefied normal butane as above set forth; these may be categorized as both technical and economical. For example, the addition of another column—the isobutane/normal butane splitter—to the process is significantly more than offset by the need for a smaller reaction vessel and a smaller, less intricate isostripping column. Furthermore, on a weight basis per unit of time, less hydrocarbon is circulated through the reaction vessel than the quantity of cooling water required to assure removal of sufficient heat of reaction to maintain the desired reaction mixture temperature.

With respect to alkylate product quality, the same is improved in view of the fact that lower reaction mixture temperatures can be maintained. Additionally, this leads to lower heat loads with respect to other equipment, and thus offers savings by virtue of lower utilities costs as well as energy conservation. Compression of the isobutane vapors from the field butane splitter permits a decreased operating pressure thereon and results in improved relative volatility for the $iC_4/nC_4$ separation. In the accompanying schematic drawing, the use of an air cooler is shown for condensing the isobutane vapors; it is contemplated, for a selected compressor size, that the full horsepower thereof will be utilized at all times. Therefore, the bottom temperature of the splitter will vary with ambient air temperature, and the reaction mixture temperature will be commensurately colder during periods of low ambient air temperature—e.g. night vs. day—with resultant additional improvement in alkylate product quality.

The exiting normal butane vapors absorb sufficient heat of reaction to operate the $iC_4/nC_4$ splitter; similarly, the cost of utilities for the isostripping column are decreased significantly. A single piece of equipment, a smaller reaction vessel, displaces two pieces of equipment, a larger reactor and the $iC_4/nC_4$ splitter reboiler.

Other beneficial advantages will become evident to those having the requisite skill in the art. Although the foregoing is directed toward the use of normal butane as the liquefied hydrocarbon being vaporized in the reaction vessel, other hydrocarbons may be employed. These preferably are those hydrocarbons which are normally vaporous at atmospheric pressure and a temperature of 60° F. (15.6° C.), including n-butane, i-butane, 2.2-dimethyl propane, n-butylene, i-butylene, cis and trans butylene, the butadienes and mixtures. Paraffins are preferred since the olefins can be more advantageously employed as components of the reactant stream.

In further describing my invention, and the process encompassed thereby, reference will be made to the accompanying drawing which is presented for the sole purpose of illustration. In the drawing, the process is presented by way of a simplified flow diagram in which details such as pumps, instrumentation and other controls, quench systems, heat-exchange and heat-recovery circuits, valving, start-up lines and similar hardware have been eliminated as non-essential to an understanding of the techniques involved. Utilization of such miscellaneous appurtenances, to modify the process as illustrated, will become evident to those possessing the requisite skill in the art of petroleum refining technology.

DESCRIPTION OF DRAWING

The drawing will be described in conjunction with a commercially-scaled unit designed for the alkylation of isobutane with a mixed olefinic feed stream, containing propylene, various butylenes and amylenes, in an exchanger type reaction vessel. This unit has a fresh olefinic feed charge rate of about 7,125 Bbl/day (1,149.79 moles/hr.), which stream has been recovered from the product effluent of a fluid catalytic cracking unit.

Combined feed, inclusive of the isobutane recycle stream recovered from the alkylate-containing effluent in line 26, and the isobutane in line 2 which is recovered from the field butane stream in line 11, is introduced into the alkylation reaction vessel 5 by way of line 1 and multiple feed conduits 3 and 4. HF-acid from acid settler 24 is withdrawn via conduit 25. A portion is diverted through conduit 7 and introduced into reactor 5 by way of multiple feed conduits 6, 7 and 8. The remainder of the HF-acid, withdrawn through line 25, continues therethrough to a regeneration vessel not illustrated herein.

In the HF alkylation unit, of which the drawing illustrates only a part, the sources of HF include the following: 139.31 moles/hr. from the isostripping column; 220.94 moles/hr. of regenerated acid; 139.31 moles/hr. from an isostripper settler; and, 70,032 moles/hr. from settler 20, for a total acid charge to reactor 6 of 70,531.56 moles/hr. Hydrocarbon sources include: the fresh olefinic feed stream, 1149.79 moles/hr.; 451.94 moles/hr. of isobutane make-up; 386.50 moles/hr. entering with the regenerated acid stream; 9,164.31 moles/hr. of isobutane-rich recycle from the isostripping column; and, 74.3 moles/hr. from $iC_4/nC_4$ splitter column 13 via line 2. The material balance around alkylation reaction vessel 5, exclusive of the HF-acid stream, is presented in the following tabulation, with the concentrations of the various components being given in terms of moles/hr. for convenience.

In reaction vessel 5, the isobutane/olefinic hydrocarbon mole ratio is about 13.0:1.0 and the HF acid/hydrocarbon volumetric ratio is about 1.5:1.0. Reaction vessel 5 is maintained at a pressure of about 233 psig. (16.9 atm.), with the HF-acid being introduced at a temperature of about 100° F. (37.8° C.).

TABLE

| Reaction Vessel Material Balance | | |
|---|---|---|
| Component | Charge | Effluent |
| Ethane | 1.20 | 1.20 |
| Propylene | 352.94 | — |
| Propane | 758.65 | 779.62 |
| Butylenes | 333.12 | 8258.10 |
| Isobutane | 8965.48 | 8258.10 |
| N-Butane | 657.30 | 663.47 |
| Amylenes | 3.59 | — |
| Isopentane | 104.59 | 128.54 |
| N-Pentane | 0.77 | — |
| Hexane-plus | 49.20 | 704.12 |
| Polymer Products | — | 0.22 |

The combined feed, entering the process via conduit 1, is at a temperature of about 90° F. (32.2° C.), while the field isobutane, in the absence of air cooler 20, is at a temperature of about 100° F. (37.8° C.). As hereinbefore set forth, HF-acid alkylation of an isoparaffin/olefin reactant mixture is highly exothermic, and must be tempered through the utilization of a cooling medium.

Product effluent is withdrawn from reaction vessel 5 through conduit 21, and introduced into mixer/soaker 22 wherein it is maintained for a period of about eight minutes. After this holding period, the product effluent is transferred via line 23 into HF acid settler 24. Settled HF acid is removed in line 25 in the amount of about 70,253.16 moles/hr. Of this amount, 70,032 moles/hr. are diverted through line 7 to serve as acid recycle to reaction vessel 5. Generally, the remaining 221.6 moles/hr. is accumulated until a sufficient quantity is available for introduction into an acid regenerator (not illustrated). The alkylate-containing, hydrocarbon-rich phase from settler 24, at a temperature of 100° F. (37.8° C.) and a pressure of about 203 psig. (1.48 atm.) is withdrawn through line 26, and consists of about 10,535.05 mole/hr. of hydrocarbons and 278.62 moles/hr. of HF-acid. This material is transferred to the isostripping column (not illustrated), from which the alkylate product is recovered, and HF-acid and unreacted isobutane are recycled as aforesaid.

As currently practiced, the reaction vessel, and particularly its cooling function, is calculated and designed with the temperature of the available cooling water being a principal consideration. With such conventional water cooling, the reactant mixture is further dependent upon the wet-bulb temperature of the air. In this illustration, the exothermic heat of reaction approximates $25.9 \times 10^6$ BTU/hour; with cooling water available at a temperature of about 85° F. (29.4° C.), about 10,420 gal./minute are required to maintain the alkylated product effluent in line 21 at a temperature of about 100° F. (37.8° C.), or about $5.2 \times 10^6$ lbs./hr.

In accordance with the present invention, liquefied normal butane in line 16, in the amount of about 175,000 lbs/hr., and at a temperature of about 90° F. (32.2° C.), is introduced through header 17 and is vaporized in tubes 18, maintaining the reactor temperature at 100° F. Normal butane vapors are withdrawn from header 19 through conduit 9 at a pressure of about 30 psig. and introduced into iC$_4$/nC$_4$ splitting column 10 at a temperature of about 90° F. Also introduced into splitter 10 is the field butane stream in line 11. The splitter 10 functions to recover substantially pure isobutane in line 13 and normal butane in conduit 15. In normal, steady operation of the illustrated system, line 12 will not be utilized; its sole purpose is to function during periods of start-up and shut-down of the unit. Thus, at lined-out conditions of operation, propane and lighter components will exit with the isobutane stream in line 13. Excess normal butane, not needed for recycle through conduit 16, continues through line 15 and is withdrawn from the process.

In accordance with the present inventive concept, the recovered isobutane in conduit 13 is increased to a pressure of about 56 psig., via compressive means 14, and continues therethrough into air cooler 20, wherein the temperature is decreased to about 100° F. (37.8° C.). Air cooler 20 is sized to perform the above-described service when cooling air is available at peak ambient daytime temperature. During periods when the ambient air temperature is lower than the daytime peak, the compressor will function at its full horsepower. For example, should the ambient air temperature drop 30° F. (16.6° C.) below the peak ambient temperature, air cooler 20 will lower the temperature of the isobutane in conduit 13 to about 70° F. (21.1° C.), and the compressor discharge pressure will decrease to approximately 30 psig. The compressor, at this reduced discharge pressure has the capability of maintaining the normal butane in line 16 at about 13 psig., corresponding to a temperature of about 70° F. (21.1° C.). During this period, the now colder normal butane is capable of maintaining the reactor temperature at 80° F. (26.7° C.), resulting in improved alkylate product quality and the other aforementioned benefits.

The foregoing, particularly when viewed in conjunction with the drawing, clearly demonstrates the method of effecting the present invention, as well as illustrates the benefits afforded through the utilization thereof.

I claim as my invention:

1. A process for the acid-catalyzed alkylation of an isoparaffin with an olefinic feed stream which comprises the steps of:
    (a) separating an isoparaffin and a normal paraffin mixture at separation conditions of temperature and pressure to provide (i) an isoparaffin concentrate and, (ii) a normal paraffin concentrate;
    (b) increasing said pressure of said isoparaffin concentrate and reducing said temperature of said isoparaffin concentrate separated from step (a);
    (c) reacting said isoparaffin from step (b) with said olefinic feed stream in admixture with an acid-acting catalyst, in a reaction vessel and at alkylation conditions selected to produce a normally liquid alkylate product;
    (d) introducing a liquefied portion of said normal paraffin concentrate into said reaction vessel and therein vaporizing said normal paraffin via heat exchange means in said vessel in contact with the reaction mixture of step (c), and
    (e) withdrawing an alkylate product from step (c).

2. The process of claim 1 further characterized in that said normal paraffin in step (a) is vaporous at atmospheric pressure and a temperature of 60° F.

3. The process of claim 1 further characterized in that said isoparaffin is isobutane.

4. The process of claim 1 further characterized in that said olefinic feed stream comprises propylene.

5. The process of claim 1 further characterized in that said olefinic feed stream comprises butylene.

6. The process of claim 1 further characterized in that said olefinic feed stream comprises propylene and butylene.

7. The process of claim 2 further characterized in that said normal paraffin is normal butane.

8. In a process for the HF-acid catalyzed alkylation of isobutane with an olefinic feed stream, in which process a field butane stream, containing normal butane and isobutane, and an alkylated reaction effluent hydrocarbon stream, containing unreacted isobutane, are separated in a common fractionation column to (i) recover the normally liquid alkylate product, (ii) remove a normal butane concentrate from said column and, (iii) provide an isobutane concentrate for recycle to the alkylation reaction zone, the improvement which comprises the steps of:
    (a) introducing said field butane stream into a separate fractionation column and therein separating said stream at separation conditions of temperature and pressure to provide (i) an isobutane concentrate and, (ii) a normal butane concentrate;
    (b) increasing said pressure of said isobutane concrete and reducing said temperature of said isoparaffin concentrate separated from step (a);

(c) reacting said isobutane with an olefinic feed stream in admixture with HF-acid, in a reaction vessel and at alkylation conditions selected to produce a normally liquid alkylate product;
(d) liquefying at least a portion of said normal butane concentrate;
(e) introducing the liquefied portion into said reaction vessel, and therein vaporizing said normal butane portion via heat exchange means in said vessel in contact with the reaction mixture of step (c).

9. The process of claim 8 further characterized in that the temperature of said isobutane concentrate is reduced through the use of ambient air.

10. The process of claim 8 further characterized in that said olefinic feed stream comprises a mixture of propylene and isobutylene.

* * * * *